United States Patent
Heinrich et al.

(10) Patent No.: US 8,579,938 B2
(45) Date of Patent: Nov. 12, 2013

(54) STAPLE FOR USE IN SURGICAL PROCEDURES

(75) Inventors: Russell Heinrich, Madison, CT (US); Robert J. DeSantis, Redding, CT (US); Richard D. Gresham, Guilford, CT (US); Kenneth M. Blier, Meriden, CT (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 13/450,753

(22) Filed: Apr. 19, 2012

(65) Prior Publication Data

US 2012/0203274 A1 Aug. 9, 2012

Related U.S. Application Data

(62) Division of application No. 12/486,819, filed on Jun. 18, 2009, now abandoned.

(60) Provisional application No. 61/082,852, filed on Jul. 23, 2008.

(51) Int. Cl.
*A61B 17/064* (2006.01)
*A61B 17/068* (2006.01)

(52) U.S. Cl.
USPC ........................................ 606/220; 227/175.1

(58) Field of Classification Search
USPC .............. 606/219, 220; 227/175.1–182.1, 19, 227/155
See application file for complete search history.

(56) References Cited

U.S. PATENT DOCUMENTS

| 352,410 | A | * | 11/1886 | Howell ........................ 227/144 |
| 3,598,299 | A | | 8/1971 | Johnson |
| 3,771,526 | A | | 11/1973 | Rudie |
| 3,837,555 | A | | 9/1974 | Green |
| 4,014,492 | A | | 3/1977 | Rothfuss |
| 4,256,251 | A | * | 3/1981 | Moshofsky .................. 227/120 |
| 4,319,576 | A | | 3/1982 | Rothfuss |
| 4,391,401 | A | * | 7/1983 | Moshofsky ..................... 227/19 |
| 4,605,001 | A | | 8/1986 | Rothfuss et al. |
| 4,608,981 | A | | 9/1986 | Rothfuss et al. |
| 4,610,383 | A | | 9/1986 | Rothfuss et al. |

(Continued)

FOREIGN PATENT DOCUMENTS

| EP | 0588081 A | 3/1994 |
| EP | 0878169 | 11/1998 |

(Continued)

OTHER PUBLICATIONS

European Search Report for EP 06016963.8-2318 date of completion is Mar. 9, 2007.

(Continued)

*Primary Examiner* — Ryan Severson
*Assistant Examiner* — Rachel S Papeika (57) ABSTRACT

A staple is provided having a backspan and a first and second legs extending distally from the backspan. Each of the first and second legs includes a bend dividing each leg into a traversing leg portion and a substantially linear clenching leg portion. A staple plate is positionable over the first and second legs between the backspan and the first and second clenching leg portions. An anvil assembly has first and second movable members which move toward to one another to engage outer surfaces of the first and second clenching leg portions. There is further disclosed a method of forming the staple through tissue.

18 Claims, 8 Drawing Sheets

(56) References Cited

U.S. PATENT DOCUMENTS

| | | |
|---|---|---|
| 4,741,336 A | 5/1988 | Failla et al. |
| 4,767,044 A | 8/1988 | Green |
| 4,809,695 A | 3/1989 | Gwathmey et al. |
| 4,848,637 A | 7/1989 | Pruitt |
| 4,881,545 A | 11/1989 | Isaacs et al. |
| 4,930,503 A | 6/1990 | Pruitt |
| 4,941,623 A | 7/1990 | Pruitt |
| 4,955,898 A * | 9/1990 | Matsutani et al. .......... 606/219 |
| 4,978,049 A | 12/1990 | Green |
| 5,027,834 A | 7/1991 | Pruitt |
| 5,108,422 A | 4/1992 | Green et al. |
| 5,180,092 A | 1/1993 | Crainich |
| 5,201,746 A | 4/1993 | Shichman |
| 5,219,353 A | 6/1993 | Garvey, III et al. |
| 5,219,359 A * | 6/1993 | McQuilkin et al. .......... 606/232 |
| 5,240,163 A | 8/1993 | Stein et al. |
| 5,282,829 A | 2/1994 | Hermes |
| 5,342,396 A | 8/1994 | Cook |
| 5,350,400 A | 9/1994 | Esposito et al. |
| 5,425,489 A * | 6/1995 | Shichman et al. .......... 227/108 |
| 5,452,836 A | 9/1995 | Huitema et al. |
| 5,452,837 A | 9/1995 | Williamson, IV et al. |
| 5,470,010 A | 11/1995 | Rothfuss et al. |
| 5,484,095 A | 1/1996 | Green et al. |
| 5,497,931 A | 3/1996 | Nakamura |
| 5,501,693 A | 3/1996 | Gravener |
| 5,509,920 A | 4/1996 | Phillips et al. |
| 5,571,116 A | 11/1996 | Bolanos |
| 5,571,285 A | 11/1996 | Chow et al. |
| 5,634,926 A | 6/1997 | Jobe |
| 5,667,526 A | 9/1997 | Levin |
| 5,667,527 A | 9/1997 | Cook |
| 5,676,674 A | 10/1997 | Bolanos et al. |
| 5,697,542 A | 12/1997 | Knodel et al. |
| 5,709,680 A | 1/1998 | Yates et al. |
| 5,741,268 A | 4/1998 | Schutz |
| 5,810,822 A | 9/1998 | Mortier |
| 5,865,361 A | 2/1999 | Milliman et al. |
| 5,871,135 A | 2/1999 | Williamson, IV et al. |
| 5,915,616 A | 6/1999 | Viola et al. |
| 5,964,394 A | 10/1999 | Robertson |
| 6,083,242 A | 7/2000 | Cook |
| 6,202,914 B1 | 3/2001 | Geiste et al. |
| 6,325,810 B1 | 12/2001 | Hamilton et al. |
| 6,348,054 B1 | 2/2002 | Allen |
| 6,786,382 B1 | 9/2004 | Hoffman |
| 6,905,057 B2 | 6/2005 | Swayze et al. |
| 6,959,852 B2 | 11/2005 | Shelton, IV et al. |
| 6,964,363 B2 | 11/2005 | Wales et al. |
| 6,978,921 B2 | 12/2005 | Shelton, IV et al. |
| 6,978,922 B2 | 12/2005 | Bilotti et al. |
| 6,988,649 B2 | 1/2006 | Shelton, IV et al. |
| 7,000,818 B2 | 2/2006 | Shelton, IV et al. |
| 7,000,819 B2 | 2/2006 | Swayze et al. |
| 7,044,352 B2 | 5/2006 | Shelton, IV et al. |
| 7,055,731 B2 | 6/2006 | Shelton, IV et al. |
| 7,059,508 B2 | 6/2006 | Shelton, IV et al. |
| 7,070,083 B2 | 7/2006 | Jankowski |
| 7,455,676 B2 | 11/2008 | Holsten et al. |
| 2002/0042621 A1 | 4/2002 | Liddicoat et al. |
| 2004/0004105 A1 | 1/2004 | Jankowski |
| 2004/0073222 A1 | 4/2004 | Koseki |
| 2004/0167573 A1 | 8/2004 | Williamson et al. |
| 2004/0232195 A1 | 11/2004 | Shelton et al. |
| 2004/0232199 A1 | 11/2004 | Shelton et al. |
| 2004/0247415 A1 | 12/2004 | Mangone, Jr. |
| 2005/0006430 A1 | 1/2005 | Wales |
| 2005/0006431 A1 | 1/2005 | Shelton et al. |
| 2005/0006434 A1 | 1/2005 | Wales |
| 2005/0023324 A1 | 2/2005 | Doll et al. |
| 2005/0023325 A1 | 2/2005 | Gresham et al. |
| 2005/0070925 A1 | 3/2005 | Shelton, IV et al. |
| 2005/0070958 A1 | 3/2005 | Swayze et al. |
| 2005/0173490 A1 | 8/2005 | Shelton, IV |
| 2005/0178813 A1 | 8/2005 | Swayze et al. |
| 2005/0187576 A1 | 8/2005 | Whitman et al. |
| 2005/0263562 A1 | 12/2005 | Shelton, IV et al. |
| 2005/0267530 A1 | 12/2005 | Cummins |
| 2006/0000868 A1 | 1/2006 | Shelton, IV et al. |
| 2006/0015144 A1 | 1/2006 | Burbank et al. |
| 2006/0022014 A1 | 2/2006 | Shelton, IV et al. |
| 2006/0022015 A1 | 2/2006 | Shelton, IV et al. |
| 2006/0025809 A1 | 2/2006 | Shelton, IV |
| 2006/0025810 A1 | 2/2006 | Shelton, IV |
| 2006/0025811 A1 | 2/2006 | Shelton, IV |
| 2006/0025812 A1 | 2/2006 | Shelton, IV |
| 2006/0025813 A1 | 2/2006 | Shelton, IV et al. |
| 2006/0025816 A1 | 2/2006 | Shelton, IV |
| 2006/0025817 A1 | 2/2006 | Ortiz et al. |
| 2006/0039779 A1 | 2/2006 | Ring |
| 2006/0049230 A1 | 3/2006 | Shelton, IV et al. |
| 2006/0097026 A1 | 5/2006 | Shelton, IV |
| 2006/0124688 A1 | 6/2006 | Racenet et al. |
| 2006/0163312 A1 | 7/2006 | Viola et al. |
| 2006/0226196 A1 | 10/2006 | Hueil et al. |
| 2006/0291981 A1 | 12/2006 | Viola et al. |
| 2007/0010838 A1 | 1/2007 | Shelton, IV et al. |
| 2008/0078800 A1 | 4/2008 | Hess et al. |

FOREIGN PATENT DOCUMENTS

| | | |
|---|---|---|
| EP | 0640315 | 12/1998 |
| EP | 1090592 | 4/2001 |
| EP | 1316290 | 6/2003 |
| EP | 1479346 | 11/2004 |
| EP | 1607048 | 12/2005 |
| EP | 1728473 A | 12/2006 |
| FR | 2838952 | 10/2003 |
| GB | 2019296 A | 10/1979 |
| GB | 2029754 A | 3/1980 |
| GB | 2051287 A | 1/1981 |
| SU | 405234 | 9/1975 |
| SU | 1333319 | 8/1987 |
| SU | 1442191 | 12/1988 |
| SU | 1459659 | 2/1989 |
| WO | WO 90/05489 | 5/1990 |
| WO | WO 97/34533 | 9/1997 |
| WO | WO 02/30296 A | 4/2002 |
| WO | WO 03/094743 | 11/2003 |
| WO | WO 03/094747 | 11/2003 |
| WO | WO 2006/055385 A | 9/2006 |

OTHER PUBLICATIONS

European Search Report for EP 09251240.9 mailed Oct. 19, 2009.
European Search Report mailed Nov. 16, 2009 in European Patent Application No. EP 09 251 793.7, filed Jul. 15, 2009.

* cited by examiner

STAPLE FOR USE IN SURGICAL PROCEDURES

CROSS REFERENCE TO RELATED APPLICATIONS

The present application is a divisional application of and claims the benefit of and priority to U.S. patent application Ser. No. 12/486,819 filed on Jun. 18, 2009 now abandoned by Heinrich et al., which claims the benefit of and priority to U.S. Provisional Application No. 61/082,852 filed on Jul. 23, 2008, the entire contents of each of these applications are herein incorporated by reference.

BACKGROUND

1. Technical Field

The present disclosure relates to a surgical staple for use in surgical procedures. More particularly, the present disclosure relates to a surgical staple and a staple assembly configured to accommodate various thicknesses of tissue by assuming a box configuration upon formation through tissue. The present disclosure also relates to a method of stapling tissues of various thicknesses with a single, uniform size staple.

2. Background of Related Art

During various surgical procedures it is often necessary to secure one or more tissue sections together or to secure auxiliary structures such as, for example, mesh, buttress material, etc. to tissue. This is typically accomplished by driving a conventional staple, having a backspan and a pair of legs extending from the backspan, through the tissue and/or through the auxiliary structure. Once the conventional staple has been driven through the tissue, the ends of the legs are engaged with an anvil of the type typically having a pair of arcuate anvil pockets. This engagement causes the ends of the legs to be bent or recurved back towards the tissue to secure the tissue sections together and/or to secure the auxiliary material to the tissue. These bent or recurved portions of the staple legs are the tissue clenching portions of the legs.

When attempting to secure relatively thick sections of tissue together or auxiliary material to a relatively thick tissue section, the sizing of the conventional staple is critical to ensure sufficient leg lengths to traverse the tissue. Insufficient leg lengths will result in incomplete stapling of the tissue.

Further, when attempting to secure relatively thin sections of tissue together, or auxiliary material to the relatively thin tissue section, the sizing of the conventional staple is selected to ensure that there is not an excess of leg length. Excess leg length may result in the clenching portions of the legs projecting substantially away from the tissue as well as causing the ends of the leg to recurve back into and penetrate the tissue.

Therefore, it is desirable to provide a staple having a leg length sufficient for various tissue thicknesses expected to be encountered. It is further desirable to provide a box shaped staple capable of being formed such that the clenching portions of the legs lie parallel to and flush against the tissue to be secured. It is still further desirable to provide a box staple assembly incorporating a staple plate to increase the bearing area of the staple against the tissue and shield the tissue from the ends of the staple legs.

SUMMARY

There is disclosed a box staple including a backspan and a first leg extending from the backspan. The first leg is divided into a first traversing leg portion and a first linear clenching leg portion by a first bend. A second leg also extends from the backspan and is divided into a second traversing leg portion and a second linear clenching leg portion by a second bend. At least one of the first and second linear clenching leg portions is oriented parallel to the backspan. In one embodiment, both the first and second linear clenching leg portions are oriented parallel to the backspan.

At least one of the first and second traversing leg portions is oriented perpendicular to the backspan. In a specific embodiment, both the first and second traversing leg portions are oriented perpendicular to the backspan.

In one embodiment, a combined length of the first and second clenching leg portions is less than an overall length of the backspan. In an alternative embodiment, the combined length of the first and second clenching leg portions is equal to an overall length of the backspan. In a specific embodiment, the combined length of the first and second clenching leg portions is greater than an overall length of the backspan.

There is also disclosed a box staple assembly for use in tissue which generally includes a backspan and first and second legs extending from the backspan. The first leg is divided into a first traversing leg portion and a first linear clenching leg portion by a first bend. The second leg is also divided into a second traversing leg portion and a second linear clenching leg portion by a second bend. A staple plate is positioned on the first and second legs between the backspan and the first and second linear clenching leg portions. At least one of the first and second linear clenching leg portions is oriented parallel to the staple plate.

The staple plate has first and second holes to receive the first and second traversing leg portions respectively. An overall length of the staple plate is greater than an overall length of the backspan and the distance between the first and second holes is substantially equal to the overall length of the backspan.

There is also disclosed a method of forming a box staple through tissue including the step of providing a box staple of having a backspan, a first leg extending from the backspan and including a first bend zone located between the backspan and a first end of the first leg, and a second the leg extending from the backspan and including a second bend zone located between the backspan and a second end of the second leg. The first and second ends of the first and second legs are driven through a tissue section. The first leg is impacted in the first bend zone with a first angled portion of a first anvil to form a first bend within the first bend zone and dividing in the first bend zone into a first traversing leg portion and a first linear clenching leg portion.

The method further includes the step of impacting the first linear clenching leg portion with a first finishing surface of the first anvil to orient the first linear clenching leg portion parallel to the backspan.

The method further includes the step of impacting the second leg in the second bend zone with a second angled portion of a second anvil to form a second bend within the second bend zone and dividing the second bend zone into a second traversing leg portion and a second linear clenching leg portion.

The second linear clenching leg portion is impacted with a second finishing surface of the second anvil to orient the second linear clenching leg portion parallel to the backspan.

In one embodiment of the disclosed method, the first and second ends are driven through tissue such that the backspan engages an upper surface of the tissue.

In a further embodiment of the disclosed method, a staple plate is positioned over the first and second legs and engages an underside of the tissue prior to the step of impacting the first leg in the first bend zone.

In a particular embodiment, the first linear clenching leg portion is oriented parallel to the staple plate.

DESCRIPTION OF THE DRAWINGS

Embodiments of the presently disclosed box staple and box staple assembly are disclosed herein with reference to the drawings, wherein.

DETAILED DESCRIPTION OF EMBODIMENTS

Embodiments of the presently disclosed box staple and box staple assembly will now be described in detail with reference to the drawings wherein like numerals designate identical or corresponding elements in each of the several views. As is common in the art, the term "proximal" refers to that part or component closer to the user or operator, i.e. surgeon or physician, while the term "distal" refers to that part or component further away from the user.

Figure 1:
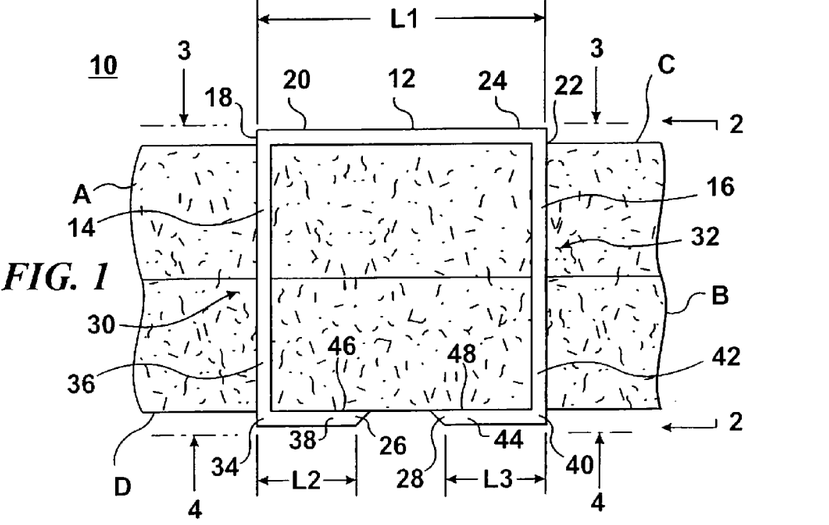
FIG. 1 is a side view, partially shown in section, of one embodiment of a disclosed box staple formed through a pair of tissue sections.
Figure 2:
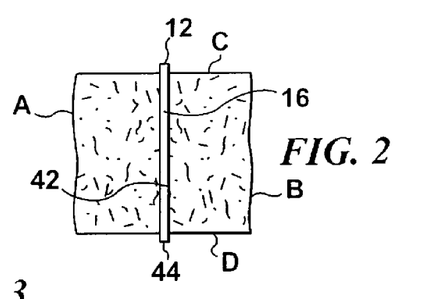
FIG. 2 is an end view taken along line 2-2 of FIG. 1.

Referring to FIG. 1-4, and initially to FIG. 1, there is disclosed an embodiment of a universal or box staple 10 for use in various thickness of tissues. Box staple 10 has the further advantage of providing uniform pressure against the underside of the tissues stapled as described in more detail hereinbelow. Box staple 10 generally includes a backspan 12 and first and second legs 14 and 16, respectively, extending distally from backspan 12. Specifically, a proximal end 18 of first leg 14 extends distally from a first end 20 of backspan 12 and a proximal end 22 of second leg 16 extends distally from a second end 24 of backspan 12. First leg 14 terminates in a tissue penetrating distal tip 26 and second leg 16 terminates in a tissue penetrating distal tip 28.

Box staple 10 is formed from a length of material having a generally rectangular cross-section. Box staple 10 can be formed from any number of biocompatible materials such as, for example, stainless steel, titanium, various malleable plastic materials, various bio-absorbable materials etc. When formed from metallic materials such as stainless steel or titanium, box staple 10 can be formed by drawing and cutting a length of metallic wire, stamping box staple 10 from a sheet of metallic material, etc. Likewise, when box staple 10 is formed from a plastic or bio-absorbable material, box staple 10 can be formed by injection molding, carving box staple 10 from a block of plastic material, etc.

As noted above, box staple 10 is designed for use in tissues of various thicknesses, such as, for example, relatively thick tissues A and B. In order to accommodate the various thickness tissues without excessive or insufficient compression of tissues A and B, first leg 14 has a first bend zone 30 which extends substantially between proximal end 18 and tissue penetrating distal tip 26 of first leg 14. Depending upon the thickness of the tissues encountered, first leg 14 can be bent at any location within bend zone 30 to accommodate those tissues. This is facilitated by the use of a pair of driven anvils as described in more detail herein below. Second leg 16 also includes a second bend zone 32 which extends substantially between proximal end 22 and tissue penetrating distal tip 28 of second leg 16.

Figure 3:
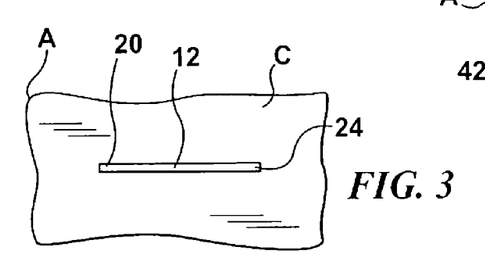
FIG. 3 is a top view taken along line 3-3 of FIG. 1.
Figure 4:
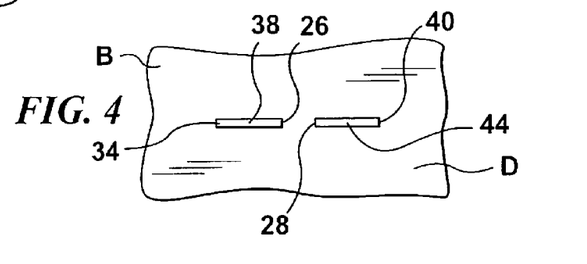
FIG. 4 is a bottom view taken along line 4-4 of FIG. 1.

When box staple 10 is fully formed through relatively thick tissues A and B, backspan 12 provides uniform compression on an upper surface C of relatively thick tissue section A (FIGS. 1 and 3). First leg 14 is formed with a first bend 34 in first transition zone 30 such that first leg 14 is divided into a first, substantially linear traversing leg portion 36 extending through relatively thick tissues A and B (FIG. 1) and a first substantially linear clenching leg portion 38 lying flush with an underside D of relatively thick tissue section B (FIGS. 1 and 4). It should be noted that, first bend 34 formed between first traversing leg portion 36 and first clenching leg portion 38 is a substantially sharp or abrupt 90° bend in contrast to the relatively gradually curving bends typically associated with prior art staples. Likewise, second leg 16 is formed with a second bend 40 in second bend zone 32 which divides second leg 16 into a second substantially linear traversing leg portion 42 extending through relatively thick tissue sections A and B (FIGS. 1 and 2) and a second substantially linear clenching leg portion 44 lying flush with underside D of relatively thick tissue section B. (FIGS. 1 and 4). Second bend 40 also forms a relatively sharp or abrupt 90° transition between second traversing leg portion 42 and second clenching like portion 44. By maintaining first and second clenching leg portions 38 and 44 in a relatively linear or straight configuration against underside D of relatively thick tissue section B, first clenching leg portion 38 and second clenching leg portion 44 maintain a uniform compression against underside D without the associated pinching or tip penetration of underside D as is common with the use of conventional staples whose leg distal ends are typically formed into a recurved shape penetrating back into the tissue.

As best shown in FIG. 1, when box staple 10 is formed through of relatively thick tissue sections A and B, the length L1 of backspan 12 is greater than or equal to the combined lengths L2 and L3 of first and second linear clenching leg portions 38 and 44, respectively.

Figure 5:
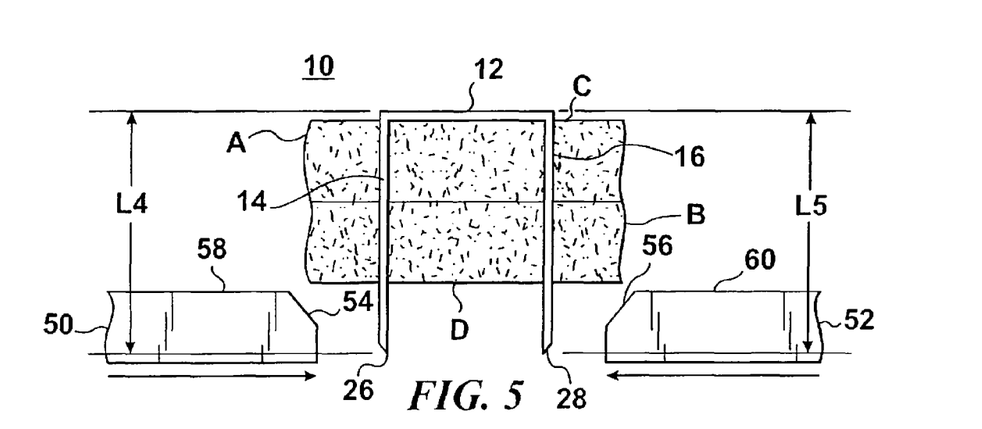
FIG. 5 is a side view, partially shown in section, of the box staple of FIG. 1, inserted through the pair of relatively thick tissue sections, immediately prior to formation.
Figure 6:
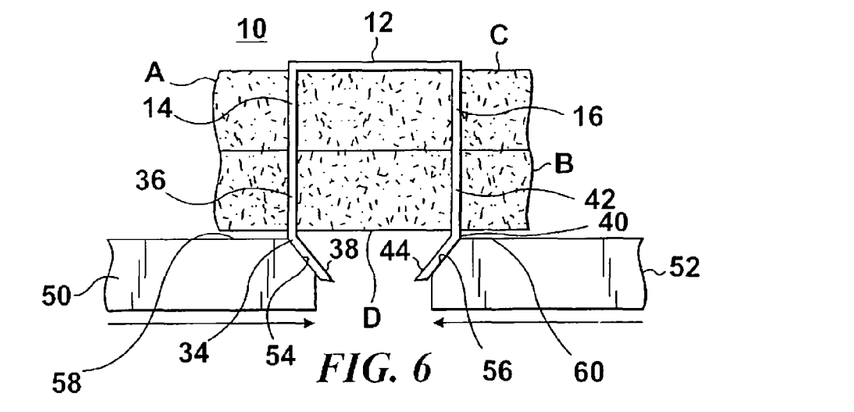
FIG. 6 is a side view similar to FIG. 5 during formation of the box staple through the pair of relatively thick tissue sections.
Figure 7:
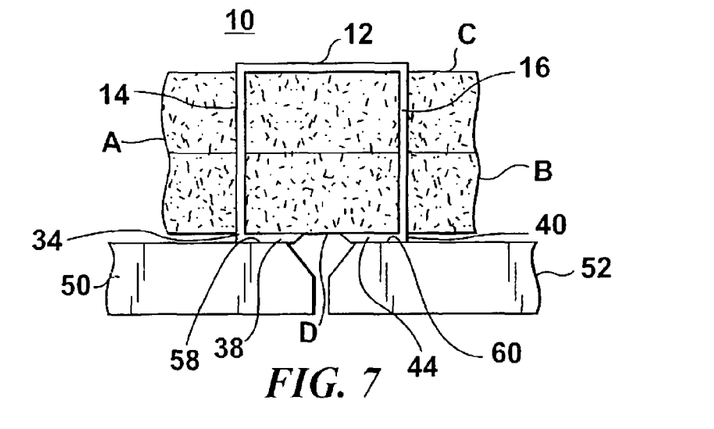
FIG. 7 is a side view similar to FIG. 6 after formation of the box staple through the pair of relatively thick tissue sections.

Referring now to FIGS. 5-7, and initially with respect to FIG. 5, the use and formation of box staple 10 with relatively thick tissue sections A and B will now be described. Initially, the dimensions of box staple 10 are chosen such that legs 14 and 16 have overall lengths L4 and L5 which are substantially greater than the anticipated combine thicknesses of any tissues to be encountered. Furthermore, each of the overall lengths L4 and L5 of first and second legs 14 and 16, respectively, is greater than half the overall length L1 of backspan 12. This ensures sufficient leg length to traverse and secure both relatively thick and thin tissue sections. Box staple 10 is initially driven through relatively thick tissue sections A and B by engaging backspan 12 with a staple driver (not shown) thereby driving first and second tissue penetrating distal tips 26 and 28, respectively, through tissue sections A and B.

Referring to FIG. 6, thereafter, a pair of anvils, such as, for example, first and second driven anvils 50 and 52, are driven laterally against first and second staple legs 14 and 16 to form box staple 10 through relatively thick tissue sections A and B. First and second driven anvils 50 and 52 generally include respective first and second angled surfaces 54 and 56 and respective first and second finishing surfaces 58 and 60. First and second angled surfaces 54 and 56 are provided to initially impact or impinge against first and second legs 14 and 16 within the respective first and second bend zones 30 and 32 to initially create first and second bends 34 and 40. This divides first bend zone 30 of first leg 14 into first traversing leg portion 36 and first linear clenching leg portion 38. Similarly, this divides second bend zone 32 into second traversing leg portion 42 and second linear clenching leg portion 44.

Referring to FIG. 7, as first and second anvils 50 and 52 are driven to the final position, first and second linear clenching leg portions 38 and 44 engaged by relatively linear finishing surfaces 58 and 60 of driven anvils 50 and 52, respectively such that first and second linear clenching leg portions 38 and 44 are brought flush into engagement with underside D of relatively thick tissue section B. As noted here in above, when box staple 10 is used in relatively thin tissue sections, the combined lengths L2 and L3 of first and second clenching leg portions 38 and 44, respectively, are substantially less than or equal to the overall length L1 of backspan 12.

Figure 8:
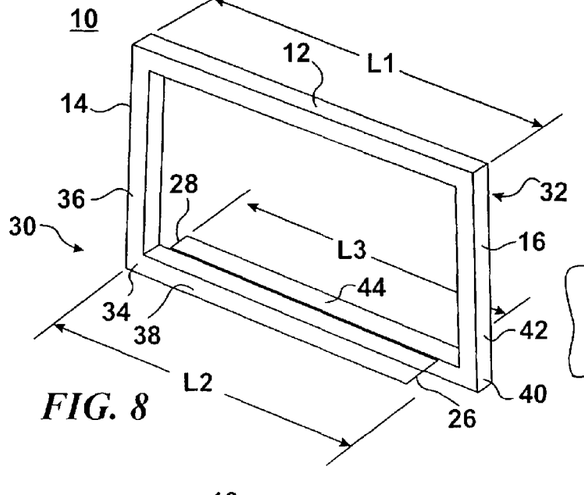
FIG. 8 is perspective view of the fully formed box staple.

Referring now to FIGS. 8-12, and initially with regard to FIG. 8, box staple 10 is illustrated in the configuration it assumes when used through a pair of relatively thin tissue sections. Specifically, when box staple 10 is formed through relatively thin tissue sections, each of the lengths L2 and L3 of respective first and second linear clenching leg portions 38 and 44 are greater than the overall length L1 of backspan 12.

Figure 9:
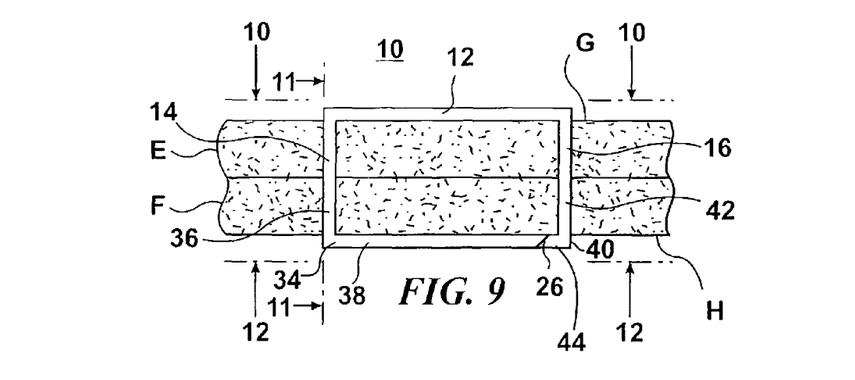
FIG. 9 is a side view, partially shown in section, of the box staple formed through a pair of relatively thin tissue sections.
Figure 10:
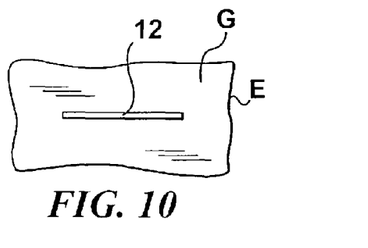
FIG. 10 is a top view taken along line 10-10 of FIG. 9.

As shown in FIG. 9, first and second traversing leg portions 36 and 42 pass through thin tissue sections E and F. First and second the linear clenching leg portions 38 and 44 lie parallel to tissue section F. As best shown in FIG. 10, backspan 12 engages an upper surface G of tissue section E while first and second linear clenching leg portions 38 and 44 engaged an underside surface H of tissue G.

Figure 11:
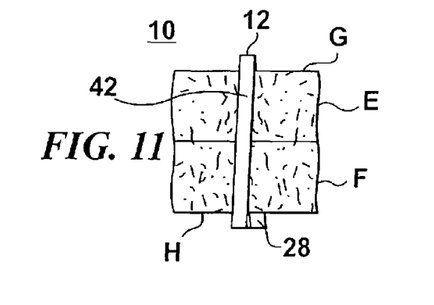
FIG. 11 is an end view taken along line 11-11 of FIG. 9.
Figure 12:
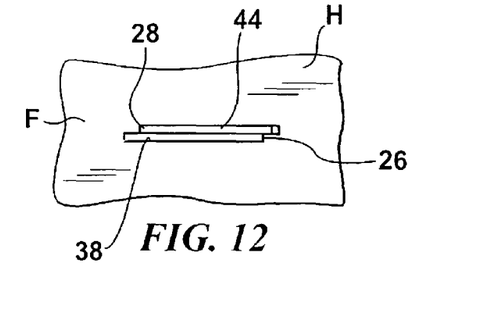
FIG. 12 is a bottom view taken along line 12-12 of FIG. 9.

As best shown in FIGS. 8, 11 and 12, the excess lengths of first and second clenching leg portions 38 and 44 are accommodated by allowing them to lie in parallel relation to each other against underside F of tissue H. Thus, box staple 10 functions as a universal staple suitable for use with both thick and thin tissue sections without risk of penetrating the tissue sections with first and second tissue penetrating distal tips 26 and 28 of respective first and second legs 14 and 16.

Figure 13:
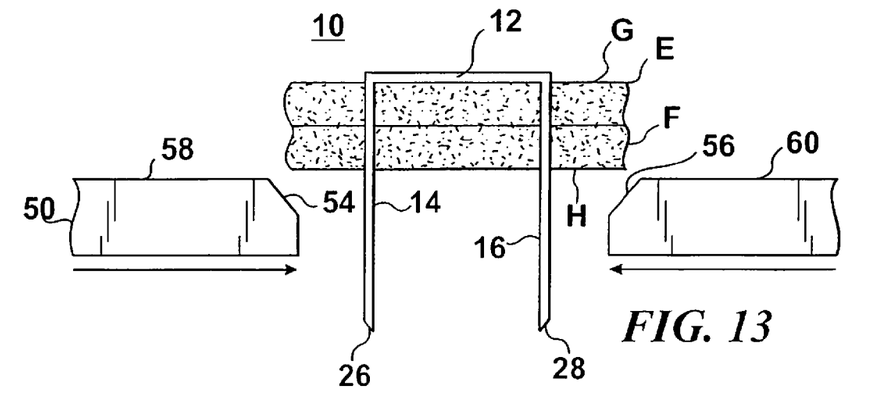
FIG. 13 is a side view, partially shown in section, of the box staple immediately prior to formation through the pair of relatively thin tissue sections.
Figure 14:
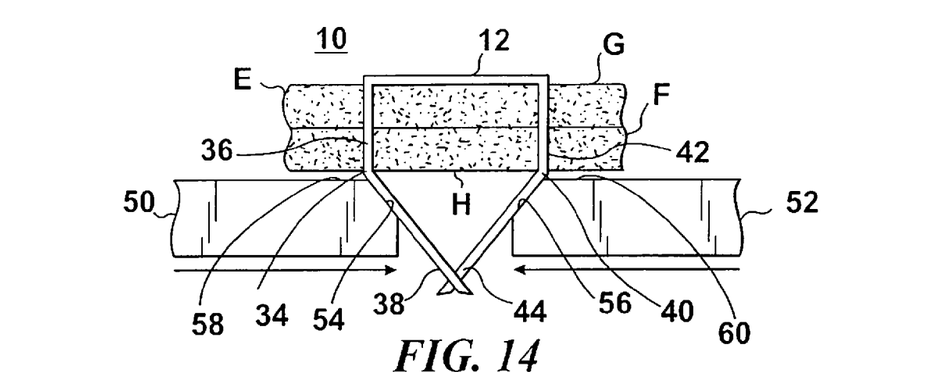
FIG. 14 is a side view similar to FIG. 13 during formation of the box staple through the pair of relatively thin tissue sections.
Figure 15:
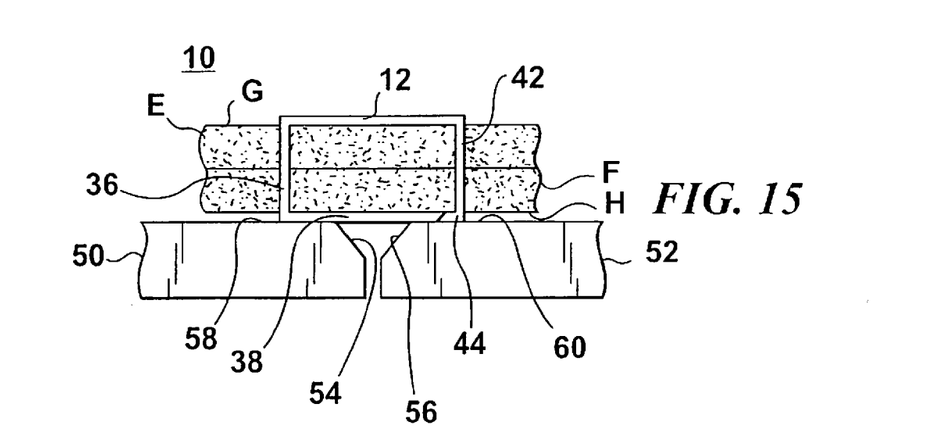
FIG. 15 is similar to FIG. 14 after formation of the box staple through the pair of relatively thin tissue sections.

Referring now to FIGS. 13-15, in order to form box staple 10 through pair of relatively thin tissue sections E and F, box staple 10 is initially driven through tissue sections E and F. Thereafter, driven anvils 50 and 52 impact staple legs 14 and 16 to initially begin to bend staple legs 14 and 16. As shown in FIG. 14, angled faces 54 and 56 of driven staples 50 and 52 initially form bends 34 and 40 to create respective first and second traversing leg portions 36 and 42 and first and second linear clenching leg portions 38 and 44. Thereafter, with reference to FIG. 15, finishing surfaces 58 and 60 of driven anvils 50 and 52 engage first and second linear clenching leg portions 38 and 44 to form first and second linear clenching leg portions 38 and 44 against underside H of tissue F and, more importantly, parallel to backspan 12. Thus, box staple 10 is particularly suited to use with relatively thin tissue sections such that first and second linear clenching leg portions 38 and 44 a lie flush against the tissue to be stapled.

Figure 16:
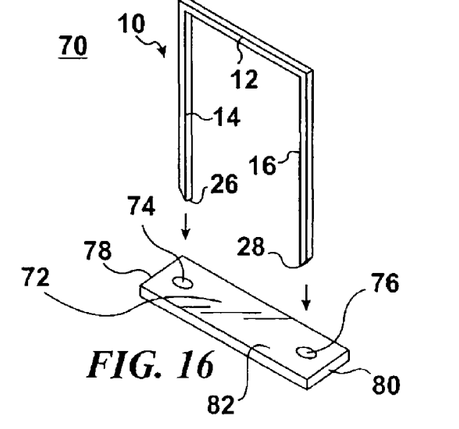
FIG. 16 is a perspective view of a box staple assembly including a box staple and a staple plate.

Referring now to FIGS. 16-20, and initially with regard to FIG. 16 there is disclosed a box staple assembly 70 including box staple 10 and a pledget or staple plate 72. Staple plate 72 increases the surface area engaging a tissue being stapled as well as protecting the tissue from engagement with staple legs 14 and 16 upon crimping of box staple 10 about tissue. Box staple 10 is as described herein above including backspan 12 and legs 14 and 16 extending from backspan 12.

Staple plate 72 is substantially rectangular having first and second holes 74 and 76 adjacent first and second ends 78 and 80, respectively, of staple plate 72. First and second holes 74 and 76 are configured to receive first and second legs 14 and 16, of box staple 10, therethrough. Staple plate 72 has an overall length L4 which is greater than the length L1 of backspan 12 (FIG. 1). Additionally, the spacing or length L5 between holes 74 and 76 is substantially identical to the length L1 of backspan 12.

Figure 17:
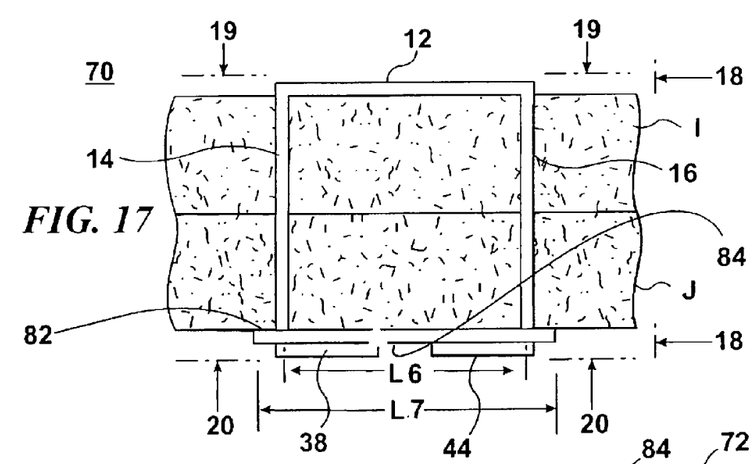
FIG. 17 is a side view, partially shown in section, of the box staple assembly formed through a pair of relatively thick tissue sections.
Figure 18:
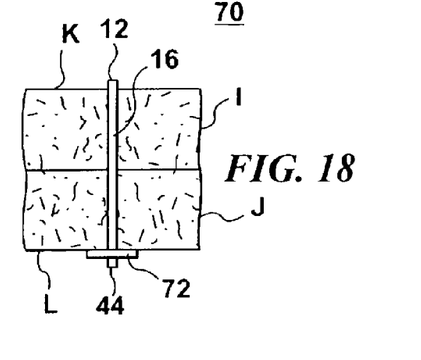
FIG. 18 is an end view taken along line 18-18 of FIG. 17.
Figure 19:
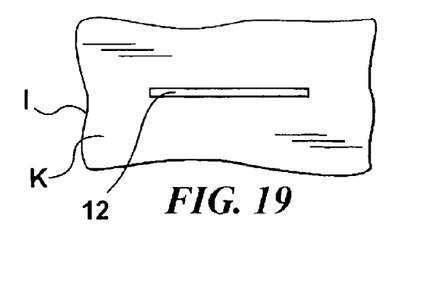
FIG. 19 is a top view taken along line 19-19 of FIG. 17.

As best shown in FIGS. 17 and 18, box staple assembly 70 is provided to secure a pair of tissue sections, such as, for example, tissue sections I and J. Backspan 12 engages an upper surface K of tissue section I (FIG. 19) while an upper surface 82 of staple plate 72 engages a lower surface L of tissue section J (FIG. 20).

Figure 20:
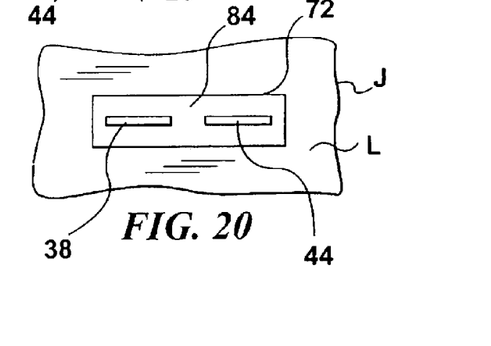
FIG. 20 is a bottom view taken along line 20-20 of FIG. 17.

Referring to FIG. 20, as noted herein above, staple plate 72 protects tissue section J from engagement with first and second clenching leg portions 38 and 44 of first and second legs 14 and 16, respectively. Specifically, upon formation of staple 10 through tissue sections I and J, staple plate 72 is interposed between tissue section J and first and second clenching leg portions 38 and 44.

Figure 21:
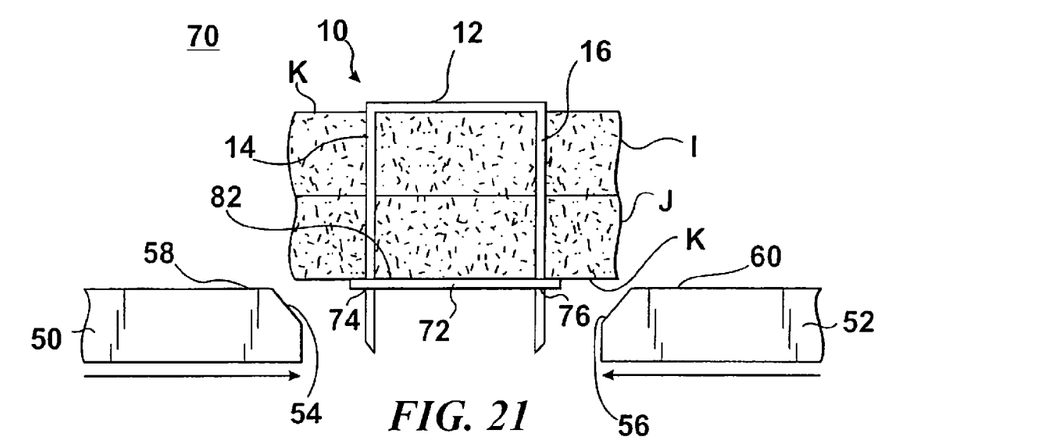
FIG. 21 is a side view, partially shown in section, of the box staple assembly immediately prior to formation through the pair of relatively thick tissue sections.
Figure 22:
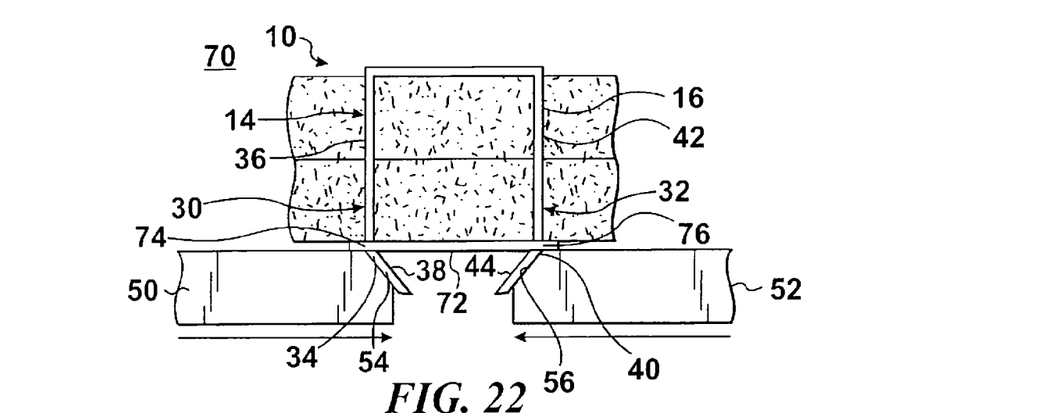
FIG. 22 is a side view, similar to FIG. 21, during formation of the box staple assembly through the pair of relatively thick tissue sections.
Figure 23:
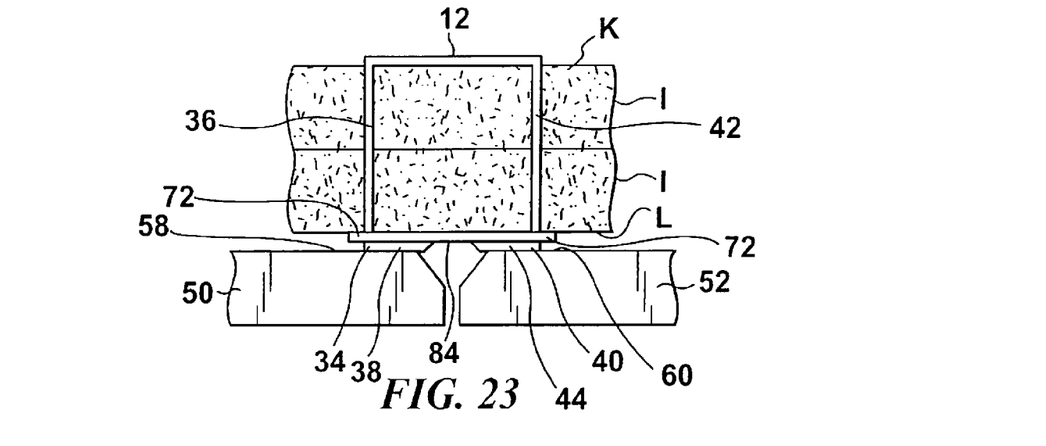
FIG. 23 is a side view, similar to FIG. 22, after formation of the box staple assembly through the pair of relatively thick tissue sections.
Figure 24:
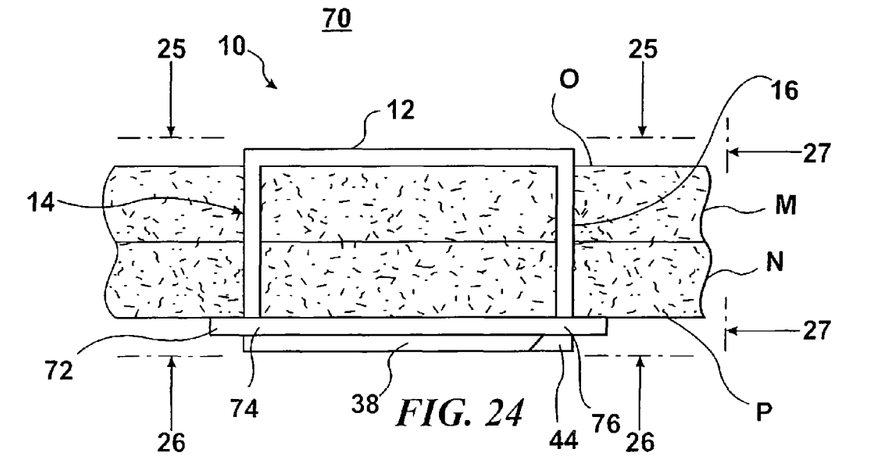
FIG. 24 is side view, partially shown in section, of the box staple assembly formed through a pair of relatively thin tissue sections.

Referring to FIGS. 21-23, the use of box staple assembly 70 to secure a pair of relatively thick tissue sections I and J together will now be described. With reference to FIG. 21, initially, box staple 10 is driven by a staple driver (not shown) toward tissue sections I and J such that first and second legs 14 and 16 penetrate tissue sections I and J until backspan 12 engages upper surface K of tissue section I. Staple plate 72 is positioned against undersurface K of tissue section J and legs 14 and 16 are extended through holes 74 and 76 a staple plate 72. This brings upper surface 82 of staple plate 72 into engagement with undersurface K of tissue section J.

With reference to FIGS. 21 and 22, thereafter, first and second driven anvils 50 and 52 are moved inwardly toward first and second legs 14 and 16. Upon engagement of first and second angled surfaces 54 and 56 with first and second legs 14 and 16, first and second legs 14 and 16 are initially bent within respective bend zones 30 and 32 to form first and second bends 34 and 40 within first and second legs 14 and 16. As noted here in above, first bend 34 divides first leg 14 into first traversing leg portion 36 and first linear clenching leg portion 36 while second bend 40 divides second legs 16 into second traversing leg portion 42 and second linear clenching leg portion 44. Notably, the extension of first and second legs 14 and 16 through first and second holes 74 and 76 in staple plate 72 facilitate forming bends 74 and 76 at substantially right angles relative to first and second traversing leg portions 36 and 38 of first and second legs 14 and 16, respectively.

Finally, with reference to FIG. 23, engagement of first and second finishing surfaces 58 and 60 of the first and second driven anvils 50 and 52 with first and second linear clenching leg portions 38 and 44 serve to secure first and second linear clenching leg portions 38 and 44 against underside 84 of staple plate 72 thereby securing staple plate 84 against underside L of tissue section J.

Figure 25:
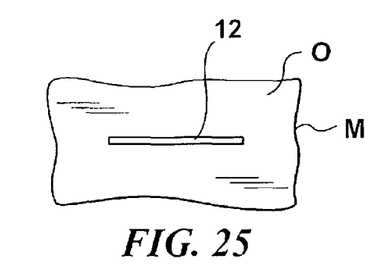
FIG. 25 is a top view taken along line 25-25 of FIG. 24.
Figure 26:
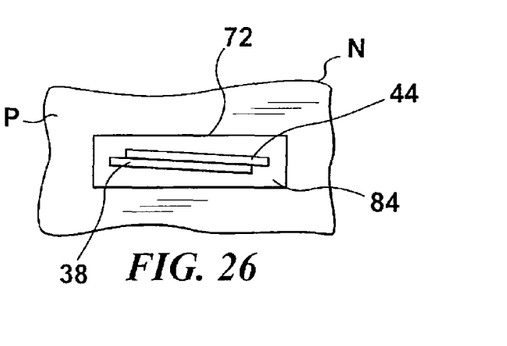
FIG. 26 is a bottom view taken along line 26-26 of FIG. 24.

Referring now to FIGS. 24-27, the use of box staple assembly 70 to secure a pair of relatively thin tissue sections, such as, for example, tissue sections M and N will now be described. The method disclosed herein with respect to relatively thin tissue sections M and N is substantially identical to the method disclosed herein above with respect to relatively thick tissue sections I and J. Initially, with reference to FIG. 24, staple 10 is driven by a staple driver (not shown) such that first and second legs 14 and 16 are driven through tissue sections M and N until backspan 12 engages an upper surface O of tissue section M (FIG. 25). First and second legs 14 and 16 are then inserted through holes 74 and 76 of staple plate 72. Thereafter, first and second driven anvils 50 and 52 (FIGS. 21-23) are moved to form first and second linear clenching leg portions 38 and 44 against underside 84 of staple plate 72 (FIG. 26).

Figure 27:
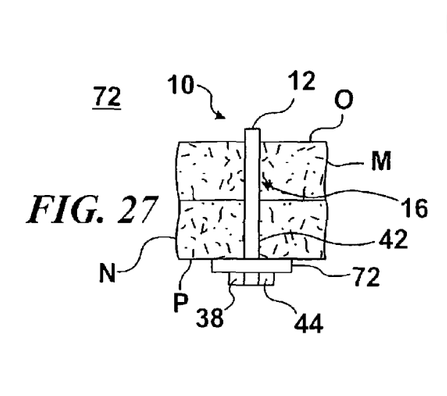
FIG. 27 is an end view taken along line 27-27 of FIG. 24.

As best shown in FIGS. 26 and 27, similar to that disclosed herein above with respect to box staple 10 in FIGS. 11 and 12, first and second linear clenching leg portions 38 and 44 are in a side-by-side and overlapping relation with respect to each other due to the excess lengths of legs 14 and 16 wine used through relatively thin tissue sections M and N. In this manner, the provision of box staple 10 having first and second legs 14 and 16 with overall lengths greater then at least the overall length of backspan 12 allows box staple 10 to function as a universal staple suitable for use with various thicknesses of tissue. As noted herein above, the provision of staple plate 72 provides additional surface bearing area against the tissue section while facilitating forming an abrupt 90° bend within first and second legs 14 and 16.

Figure 28:
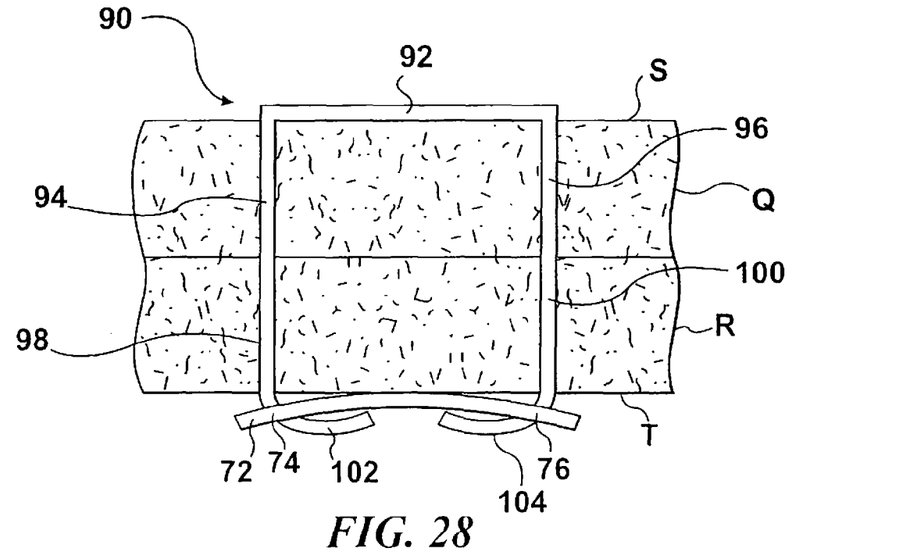
FIG. 28 is a side view, partially shown in section, of an alternate embodiment of a staple assembly including a staple and an arcuate staple plate formed through a pair of relatively thick tissue sections.
Figure 29:
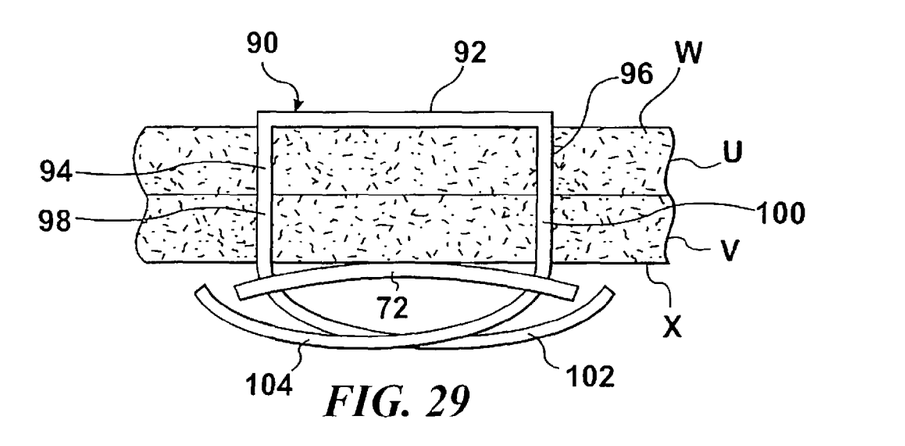
FIG. 29 is a side view, partially shown in section, of the staple assembly of FIG. 28 formed through a pair of relatively thin tissue sections.

Referring now to FIGS. 28 and 29, while staple plate 72 has been disclosed for use with box staple 10, staple plate 72 may be formed of a material which allows staple plate 72 to be used with a staple and 90 similar to box staple 10 in situations wherein staple 90 is formed with conventional anvils. As used herein, the term "conventional anvils" refers to those anvils having arcuate anvil pockets resulting in arcuate rather than linear clenching leg portions in the formed staple.

For example, with reference to FIG. 28, staple 90 includes a backspan 92 having first and second legs 94 and 96 extending from backspan 92. In use, staple 90 is driven through relatively thick tissue sections Q and R resulting in first and second traversing leg portions 98 and 100 extending through tissue sections Q and R while backspan 92 engages an upper surface S of tissue section Q. First and second legs 94 and 96 are extended through holes 74 and 76 in staple plate 72 and are clenched against staple plate 72 by arcuate anvil pockets formed in an anvil associated with a conventional stapler (not shown).

Similarly, with reference to FIG. 29, when used in conjunction with relatively thin tissue sections U and V, backspan 92 engages an upper surface W of tissue section U while traversing leg portions 98 and 100 extending through tissue sections U and V. Staple plate 72 bears against an undersurface X of tissue section V. First and second linear clenching leg portions 102 and 104 of first and second legs 94 and 96 are formed into a roughly arcuate overlapping relation due to the excess length of legs 94 and 96.

It will be understood that various modifications may be made to the embodiments disclosed herein. For example, the legs of the disclosed box staple maybe heat treated at specific points to facilitate the formation of the abrupt 90° bend between the traversing portion of the leg and the linear clenching portion of the leg. Further, alternative embodiments of anvils may be provided to form the substantially right angle within their respective legs. Additionally, the disclosed box staple may be formed from any shape memory alloy such that the right angle between the traversing leg portion and the linear clenching leg portion is formed at a predetermined location along the length of the leg. Therefore, the above description should not be construed as limiting, but merely as exemplifications of particular embodiments. Those skilled in the art will envision other modifications within the scope and spirit of the claims appended hereto.

What is claimed is:

1. A combination staple assembly and anvil assembly for use in tissue comprising:
 a staple assembly including:
  a backspan;
  a first leg being divided into a first traversing leg portion and a first substantially linear clenching leg portion by a first bend;
  a second leg being divided into a second traversing leg portion and a second substantially linear clenching leg portion by a second bend;
  a staple plate positionable on the first and second legs between the backspan and the first and second clenching leg portions; and
 an anvil assembly including first and second moveable anvil members configured to move towards one another and simultaneously engage outer surfaces of the corresponding first and second clenching leg portions of said first and second legs to form said first and second clenching leg portions substantially abutting an exterior surface of said staple plate.

2. The combination staple assembly and anvil assembly as recited in claim 1, wherein both the first and second linear clenching leg portions are oriented substantially parallel to the backspan.

3. The combination staple assembly and anvil assembly as recited in claim 1, wherein at least one of the first and second traversing leg portions is oriented substantially perpendicular to the backspan.

4. The combination staple assembly and anvil assembly as recited in claim 3, wherein both the first and second traversing leg portions are oriented substantially perpendicular to the backspan.

5. The combination staple assembly and anvil assembly as recited in claim 1, wherein the first and second bends are substantially 90 degrees.

6. The combination staple assembly and anvil assembly as recited in claim 1, wherein a combined length of the first and second clenching leg portions is less than an overall length of the backspan.

7. The combination staple assembly and anvil assembly as recited in claim 1, wherein a combined length of the first and second clenching leg portions is equal to an overall length of the backspan.

8. The combination staple assembly and anvil assembly as recited in claim 1, wherein a combined length of the first and second clenching leg portions is greater than an overall length of the backspan.

9. The combination staple assembly and anvil assembly as recited in claim 1, wherein the staple plate has first and second holes to receive the first and second traversing leg portions respectively.

10. The combination staple assembly and anvil assembly as recited in claim 9, wherein the distance between the first and second holes is substantially equal to an overall length of the backspan.

11. The combination staple assembly and anvil assembly as recited in claim 9, wherein the staple plate has an arcuate top surface.

12. The combination staple assembly and anvil assembly as recited in claim 1, wherein an overall length of the staple plate is greater than an overall length of the backspan.

13. The combination staple assembly and anvil assembly as recited in claim 1, wherein the first and second movable anvil members include corresponding first and second angled surfaces that are configured to engage the corresponding outer surfaces of the first and second clenching leg portions.

14. The combination staple assembly and anvil assembly as recited in claim 13, wherein the first and second movable anvil members include corresponding first and second finishing surfaces that are configured to secure the corresponding first and second clenching leg portions against an underside of the staple plate.

15. The combination staple assembly and anvil assembly as recited in claim 14, wherein the finishing surfaces are relatively linear.

16. The combination staple assembly and anvil assembly as recited in claim 1, wherein the first and second movable anvil members include corresponding first and second finishing surfaces that are configured to secure the corresponding first and second clenching leg portions against an underside of the staple plate.

17. The combination staple assembly and anvil assembly as recited in claim 1, wherein the first and second movable anvil members are moved laterally to engage the outer surfaces of the first and second clenching leg portions.

18. The combination staple assembly and anvil assembly as recited in claim 1, wherein the first and second clenching leg portions lie in substantially parallel relation to each other in a formed condition.

* * * * *